United States Patent
Remeijer et al.

(10) Patent No.: US 8,421,038 B2
(45) Date of Patent: Apr. 16, 2013

(54) METHODS AND SYSTEMS FOR PROTECTING CRITICAL STRUCTURES DURING RADIATION TREATMENT

(75) Inventors: Peter Remeijer, Amsterdam (NL); Marcel van Herk, Amsterdam (NL); Jan-Jakob Sonke, Amsterdam (NL); Angelo Mencarelli, Leiden (NL); Simon van Kranen, Haarlem (NL)

(73) Assignee: Elekta AB, Stockholm (SE)

( * ) Notice: Subject to any disclaimer, the term of this patent is extended or adjusted under 35 U.S.C. 154(b) by 140 days.

(21) Appl. No.: 13/166,957

(22) Filed: Jun. 23, 2011

(65) Prior Publication Data

US 2012/0326057 A1    Dec. 27, 2012

(51) Int. Cl.
    *A61N 5/00*     (2006.01)
(52) U.S. Cl.
    USPC ............ 250/492.1; 600/1; 600/3; 600/411; 600/427; 600/431; 378/4; 378/5; 378/7; 378/8; 378/19; 378/65; 378/95; 703/11
(58) Field of Classification Search ............ 250/492.2, 250/492.1; 600/1, 3, 411, 427, 431; 378/4, 378/5, 7, 8, 19, 65, 95; 703/11
See application file for complete search history.

(56) References Cited

U.S. PATENT DOCUMENTS

| | | | |
|---|---|---|---|
| 6,038,283 A * | 3/2000 | Carol et al. | 378/65 |
| 7,801,349 B2 * | 9/2010 | Wang et al. | 382/131 |
| 2011/0069815 A1 * | 3/2011 | Nord et al. | 378/65 |
| 2012/0310615 A1 * | 12/2012 | Moore et al. | 703/11 |

OTHER PUBLICATIONS

Nagel, et al., "Online dose-guided setup correction protocol for hypo fractionated lung radiotherapy," abstract, 2009, 1 page.
Mencarelli, et al., "A Dosimetric Method to derive optimal couch corrections in the presence of anatomical deformations for H & N cancer," abstract, 2011, 2 pages.

* cited by examiner

*Primary Examiner* — Jack Berman
*Assistant Examiner* — Meenakshi Sahu
(74) *Attorney, Agent, or Firm* — Goodwin Procter LLP

(57) ABSTRACT

Methods and systems are provided for protecting a critical structure during the administration of radiation treatment to a patient. A register receives proposed positions for one or more radiation beams with respect to a critical structure. A processor predicts a cumulative dose volume for the critical structure based on the dose distribution, and determines if the cumulative dose volume exceeds a tolerance value. If the cumulative dose volume exceeds the tolerance value, the dose distribution may be translated at least in part based on a relationship between the cumulative dose volume and the dose distribution position.

18 Claims, 14 Drawing Sheets

METHODS AND SYSTEMS FOR PROTECTING CRITICAL STRUCTURES DURING RADIATION TREATMENT

TECHNICAL FIELD

This invention relates to methods and systems for protecting critical structures during the administration of radiation treatment to a patient and, more particularly, to methods and systems for adjusting a proposed dose distribution.

BACKGROUND INFORMATION

Tumors and lesions are pathological anatomies characterized by abnormal growth of tissue resulting from a progressive, uncontrolled multiplication of cells, while serving no physiological function. Pathological anatomies can be treated with invasive procedures, such as surgery, but these procedures can be risky and/or harmful for the patient.

A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a tumor site from multiple angles. As the angle of the radiation source changes, each beam passes through the tumor site, but travels through a different area of healthy tissue on its way to the tumor. Ideally, the cumulative radiation dose at the tumor is high and the radiation dose to healthy tissue is low.

Radiation therapy typically includes a planning phase in which locations for the radiation beams are determined, and a treatment phase in which the radiation beams are administered. During the planning phase, a software package may be used to import three-dimensional (3-D) images, such as computerized x-ray tomography (CT) scans, for delineating structures to be targeted or avoided during treatment. A goal of the planning phase is to identify a dose distribution (i.e., a collection of radiation beams) that conforms to the tumor, while avoiding critical structures or organs at risk, such as the spinal cord or healthy brain tissue.

During the treatment phase and just prior to the administration of radiation, 3-D images may again be collected to determine whether the tumor has undergone morphological changes and/or moved with respect to nearby critical structures. To account for any changes that have occurred, the dose distribution identified during the planning phase may need to be moved, adjusted, and/or completely reworked. For example, with one approach, the proposed dose distribution is moved until it falls outside of exclusion zones placed around the critical structures. With another approach, the shape of the dose distribution is changed (e.g., by adjusting the shapes and/or relative positions of the radiation beams) until the dose distribution does not contact or intersect critical structures. Unfortunately, adjusting the proposed dose distribution can be a time consuming and expensive process.

Accordingly, a need exists for methods and systems that allow a proposed dose distribution, identified during the planning phase, to be utilized during the treatment phase with a minimal amount of adjustment, despite morphological changes and/or movements that may have occurred between a tumor and one or more critical structures.

SUMMARY OF THE INVENTION

The present invention provides methods and systems for protecting anatomical structures during the administration of radiation treatment to a patient. In certain embodiments, a proposed dose distribution is identified during a planning phase and stored in a register. During a treatment phase, a processor receives the dose distribution from the register and predicts a radiation exposure (e.g., a cumulative dose volume) for one or more critical structures. If the predicted radiation exposure is too high, the dose distribution is translated until the predicted radiation is below an acceptable threshold.

The methods and systems provided herein simplify the process of utilizing a proposed dose distribution, identified during the planning phase, for treatment during the treatment phase. Identifying a dose distribution during the planning phase can be an expensive, time consuming, and computationally intensive process. Further adjustments to the dose distribution immediately prior to treatment involve additional cost, time, and effort. The methods and systems provided herein advantageously allow the proposed dose distribution to be utilized during treatment with a minimal amount of adjustment.

In one aspect, a method is provided for protecting a critical structure during the administration of radiation treatment to a patient. The method includes the steps of (a) receiving, from a register, proposed positions for one or more radiation beams with respect to a critical structure, wherein a combination of the one or more radiation beams defines a dose distribution having a dose distribution position, and, at a processor, (b) predicting a cumulative dose volume for the critical structure based on the dose distribution, wherein the cumulative dose volume comprises a volume of the critical structure that is predicted to receive more than a specified radiation dose, (c) determining if the cumulative dose volume exceeds a tolerance value, and (d) if the cumulative dose volume exceeds the tolerance value, translating the dose distribution at least in part based on a relationship between the cumulative dose volume and the dose distribution position.

In certain embodiments, the translating step includes determining a direction in which to translate the dose distribution with respect to the critical structure, wherein the direction requires a minimum amount of translation to achieve a cumulative dose volume equal to the tolerance value. The translating step may include translating the dose distribution in the direction until the cumulative dose volume is equal to the tolerance value. In one embodiment, the translating step includes translating the dose distribution in a direction of a greatest rate of decrease in cumulative dose volume. In another embodiment, the translating step includes translating the dose distribution in a hybrid direction, wherein the hybrid direction lies between (i) a direction requiring a minimum amount of translation to achieve a cumulative dose volume equal to the tolerance value, and (ii) a direction of a greatest decrease in cumulative dose volume. The relationship between the cumulative dose volume and the dose distribution position may be determined by translating the dose distribution to proposed locations and calculating the cumulative dose volume at each proposed location. Subsequent to translating the dose distribution, the dose distribution may intersect the critical structure. The method may also include the step of generating an alert indicating that the predicted radiation exposure exceeds the tolerance value, which may be greater than zero.

In another aspect, a system is provided for protecting a critical structure during the administration of radiation treatment to a patient. The system includes a register configured to store proposed positions for one or more radiation beams with respect to at least one critical structure, wherein a combination of the one or more radiation beams defines a dose distribution having a dose distribution position. The system also includes a processor configured to (i) predict a cumulative dose volume for the critical structure based on the dose distribution, wherein the cumulative dose volume comprises a volume of the critical structure that is predicted to receive more than a specified radiation dose, (ii) determine if the cumulative dose volume exceeds a tolerance value, and (iii) if the cumulative dose volume exceeds the tolerance value, translate the dose distribution at least in part based on a relationship between the cumulative dose volume and the dose distribution position.

In certain embodiments, the processor is configured to determine a direction in which to translate the dose distribution with respect to the critical structure, wherein the direction requires a minimum amount of translation to achieve a cumulative dose volume equal to the tolerance value. The processor may also be configured to translate the dose distribution in the direction until the cumulative dose volume is equal to the tolerance value. In one embodiment, the processor is configured to translate the dose distribution in a direction of a greatest rate of decrease in cumulative dose volume. In another embodiment, the processor is configured to translate the dose distribution in a hybrid direction, wherein the hybrid direction lies between (i) a direction requiring a minimum amount of translation to achieve a cumulative dose volume equal to the tolerance value, and (ii) a direction of a greatest decrease in cumulative dose volume. To determine the relationship between the cumulative dose volume and the dose distribution position, the processor may be configured to translate the dose distribution to proposed locations and calculate the cumulative dose volume at each proposed location. Subsequent to translation of the dose distribution, the dose distribution may intersect the critical structure. The processor may be further configured to generate an alert indicating that the predicted radiation exposure exceeds the tolerance value, which may be greater than zero.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
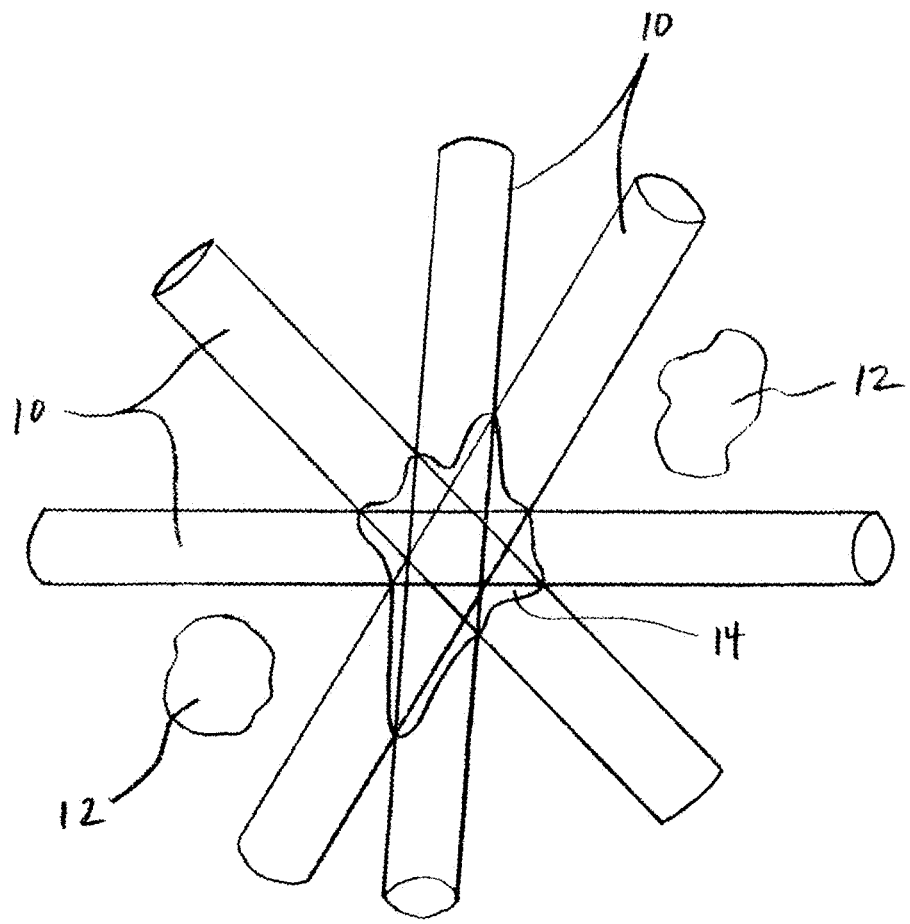
FIG. 1 is a schematic view of multiple radiation beams, a dose distribution, and critical structures, in accordance with one embodiment of the invention.

Referring to FIG. 1, in certain embodiments, methods and systems are provided for treating a target, such as a tumor or lesion, in a patient with one or more beams 10 of radiation. As depicted, the one or more beams 10 may project onto the target from different angles. The one or more beams may avoid critical structures 12 and produce a three-dimensional dose distribution 14, positioned over the target. Positions and angles for the one or more beams 10 may be proposed during a planning phase. A few days or weeks later, the proposed beams may be administered to the patient during a treatment phase, following any necessary adjustments.

In one embodiment, during the treatment planning phase, images are obtained to identify the size, shape, and placement of the target and any surrounding tissue or organs, including critical structures 12. The images may be represented in two or three dimensions, and generated using one or more techniques known in the art, such as three-dimensional ultrasound imaging, CT scanning, magnetic resonance imaging, and/or PET scanning. Based on the shapes and positions of the target and any critical structures, a proposed position and shape for the dose distribution may be identified.

Determining the shapes and positions of the radiation beams 10 to generate the proposed dose distribution 14 may be an expensive and computationally intensive process. Beam shapes may be generated that represent maximum projected shapes of the target for each planned beam direction. Identifying beam shapes and directions may be repeated any number of times, until the physician or other dosimetry specialist is satisfied that the treatment plan is appropriate and that the prescribed dose may be delivered to the target while sparing the health of surrounding structures.

Figure 2:
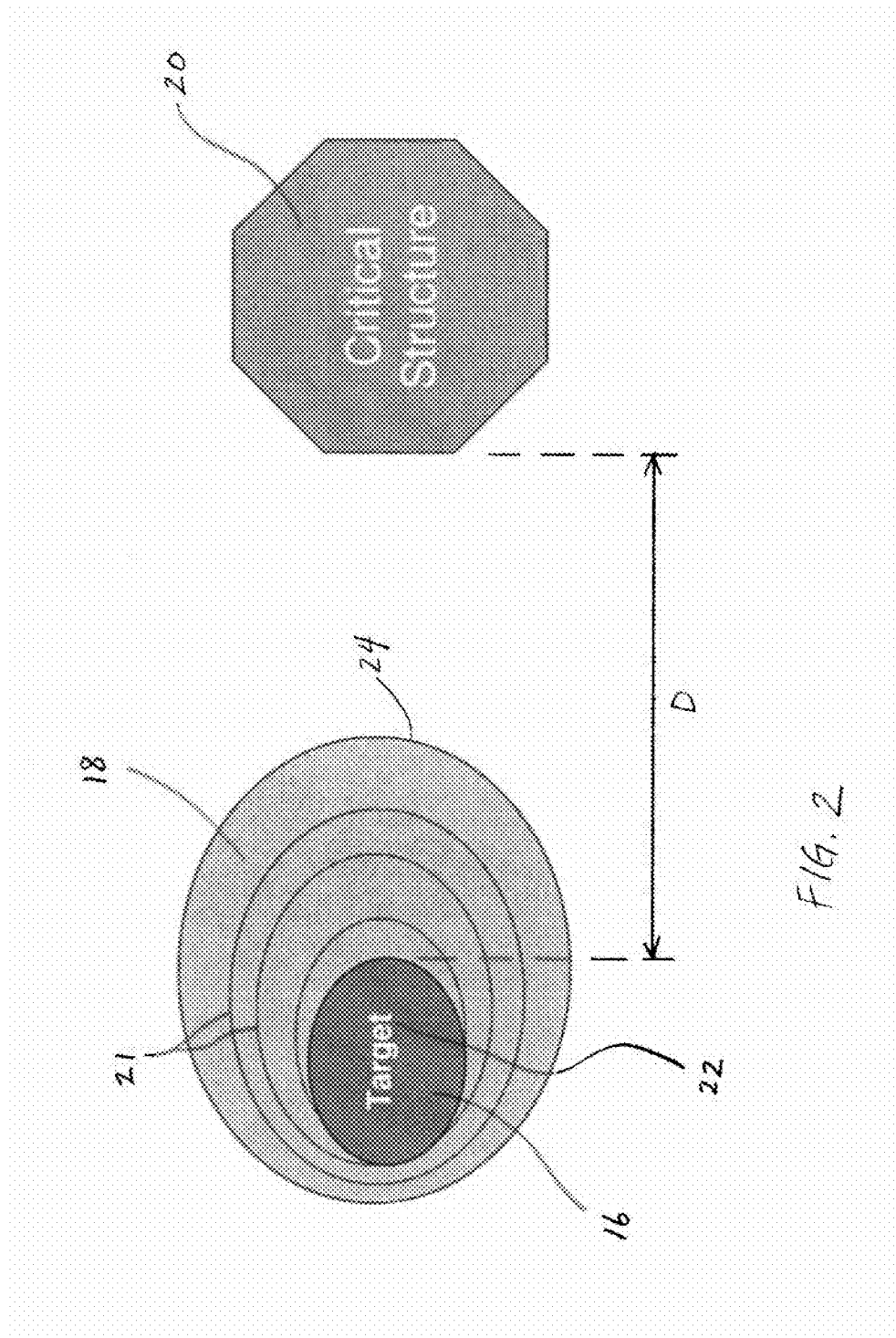
FIG. 2 is a schematic, cross-sectional view of a target, a dose distribution, and a critical structure, during a planning phase, in accordance with one embodiment of the invention.

FIG. 2 is a schematic, cross-sectional view of a target 16, a dose distribution 18, and a critical structure 20, obtained from an image of a patient during the planning phase, in accordance with an embodiment of the invention. The target 16 may be any anatomical feature such as a cancerous organ, tumor, or lesion, such as a lymph node in the neck region, a cancerous prostate, a tumor bed in a breast, or a lung tumor. As depicted, the dose distribution 18 includes isocontours 21 of constant radiation intensity. The radiation intensity may be greatest at an isocenter 22 of the dose distribution 18 and lowest at an outer edge 24 of the dose distribution 18. In the depicted embodiment, a spacing D between the target 16 and the critical structure 20 is sufficiently large and allows the dose distribution 18 to be positioned over the target 16 without contacting the critical structure 20.

As described above, the target 16 and surrounding tissue and organs can move and/or undergo morphological changes between the planning phase and the treatment phase, and/or between treatment sessions (i.e., inter-fraction movements or changes). Some targets, such as lung tumors, may move within a single treatment session (i.e., intra-fraction movements). In some instances, the treatment sessions can occur over a period of weeks or even months, giving rise to further uncertainties in patient positioning and physiology. In addition, the planning phase may occur substantially before the treatment phase or, in some cases, immediately preceding the treatment phase. As the time span increases between the phases, the target has a greater opportunity to grow, morph, and/or change its positioning with respect to surrounding normal tissue and healthy organs, thus resulting in a need for positional compensation or dose distribution adjustment.

Due to breathing and other movements within the lungs, the location of a lung tumor with respect to adjacent tissues can be especially difficult to track and identify. Various measures have been developed to mitigate this difficulty. For example, intra-fraction motion of lung tumors may be mitigated by analyzing a patient's internal anatomy during free-breathing. In addition, treatments may be based on estimated tumor position, using gating, breath hold, or average tumor position over the course of the breathing cycle. In the case of inter-fraction motion, x-ray images of the patient may be taken prior to the start of a treatment session. The images may then be analyzed for movement of the tumor position, and the patient or patient support may be repositioned, if necessary, to bring the tumor back into a desired position. Care must be taken when repositioning the patient, however, as the positional relationship between the tumor and nearby critical structures may also change. It is important that the radiation dose to nearby critical structures is not unnecessarily increased by corrective movements of the patient in treatment setup.

Prior to a radiation treatment session, the technician obtains updated images, such as three-dimensional ultrasound images, of the target 16 and surrounding tissue that characterize the most current position and shape of the target 16. The proposed dose distribution 18 may then be superimposed onto the target 16 to determine whether any adjustments to the dose distribution 18 are required.

Figure 3:
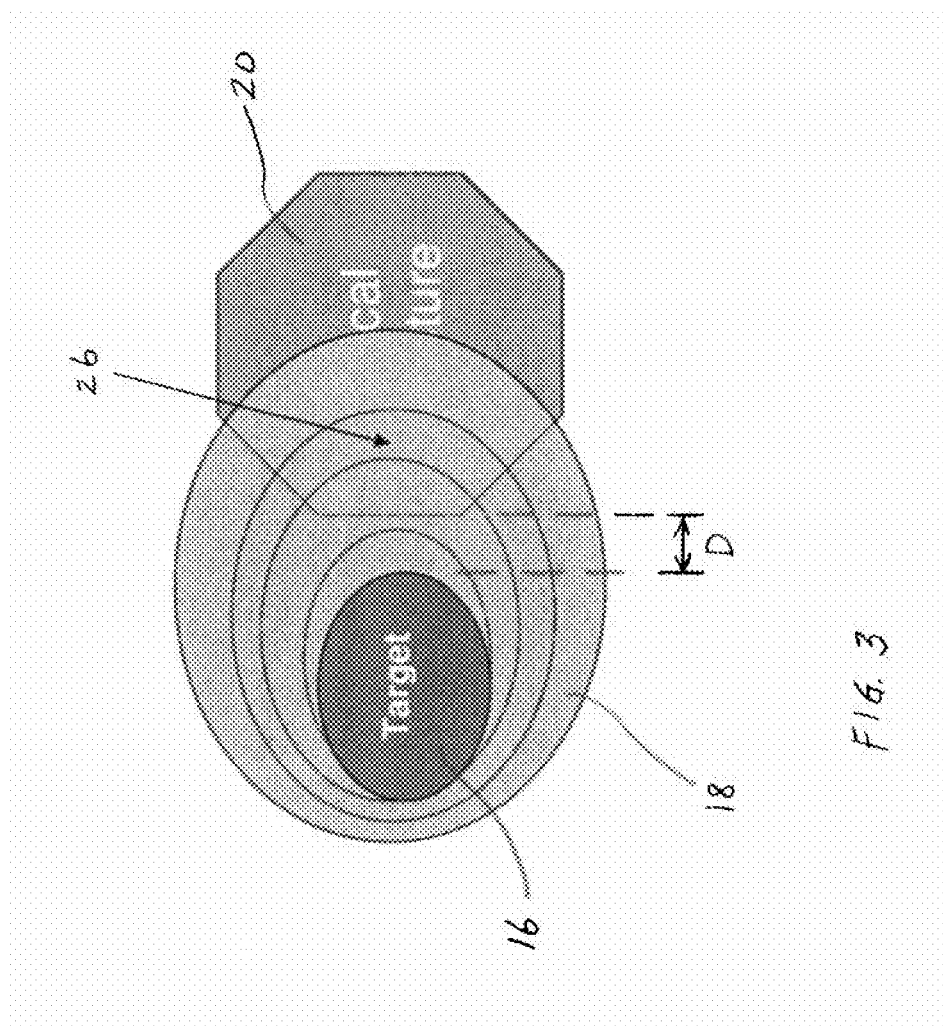
FIGS. 3 and 4 are schematic, cross-sectional views of a target, a dose distribution, and a critical structure, during a treatment phase, in accordance with one embodiment of the invention.

FIG. 3 is a schematic, cross-sectional view of the target 16, the dose distribution 18, and the critical structure 20, obtained from an image of the patient during the treatment phase. Comparing FIGS. 2 and 3, it may be seen that the spacing D between the target 16 and the critical structure 20 decreased during the time between the planning phase and the treatment phase. As a result, when the proposed dose distribution 18 is positioned over the target 16, the dose distribution 18 forms a region of contact 26 with the critical structure 20. Administering the proposed dose distribution 18 in this situation may expose the critical structure to excessive radiation.

Figure 4:
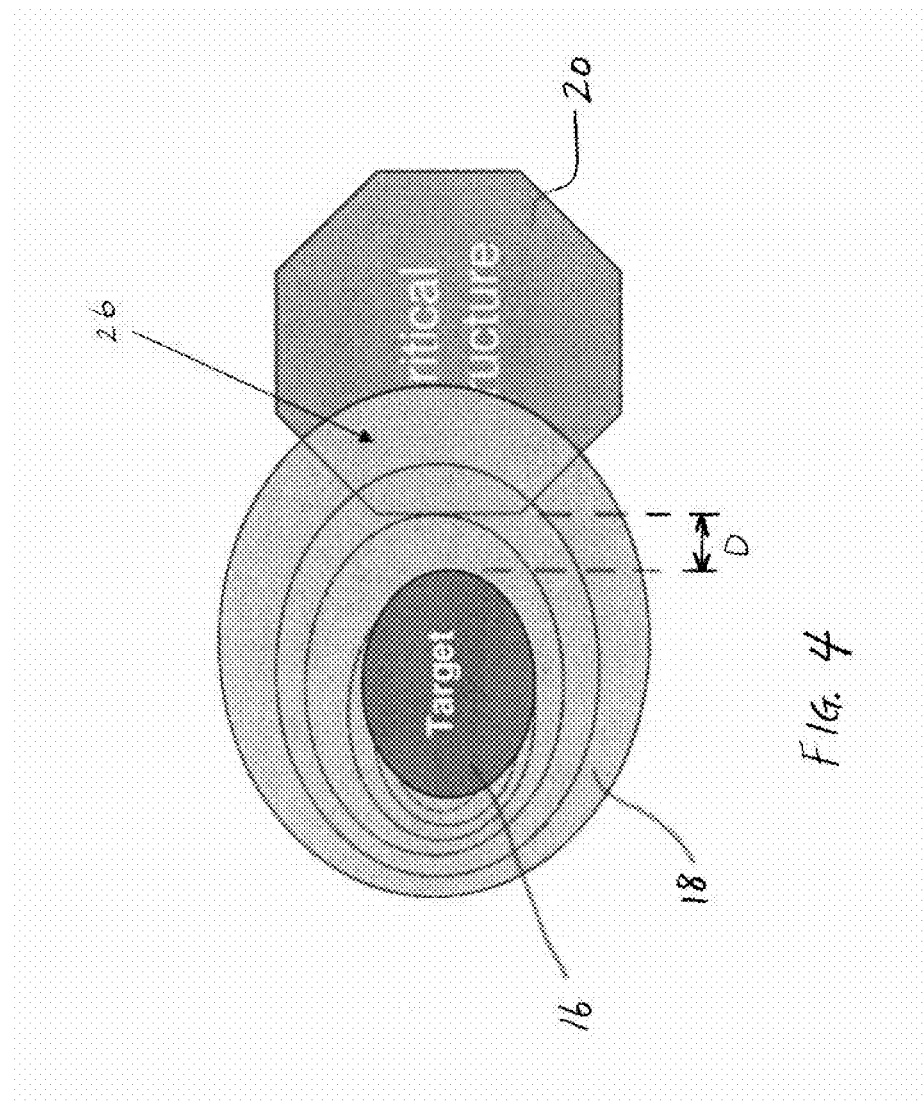

Referring to FIG. 4, in certain embodiments, methods and systems are provided for adjusting the proposed dose distribution 18 from the planning phase so that the target 16 receives an adequate dose and the critical structure 20 receives a dose that is below an acceptable threshold value. As depicted, in one embodiment, the methods and systems achieve this result by translating the dose distribution 18 away from the critical structure 20 until the dose to the critical structure 20 is acceptable. Translating the dose distribution may include maintaining a shape of the dose distribution 18 (e.g., by maintaining the shapes and sizes of the radiation isocontours 21) and/or rotating the dose distribution 18. As the dose distribution 18 is moved away from the critical structure 20, the region of contact 26 between the dose distribution 18 and the critical structure 20 may decrease.

In certain embodiments, the acceptable threshold value for the critical structure 20 may be any value that results in an acceptable dose to the critical structure 20. For example, the threshold value may be less than about 2000 cGy, less than about 1000 cGy, less than about 500 cGy, less than about 200 cGy, less than about 100 cGy, or less than about 50 cGy. In one embodiment, the threshold value is greater than zero. For example, when the dose distribution 18 has been translated to an acceptable location, the dose distribution 18 may contact or intersect at least a portion of the critical structure 20.

Figure 5:
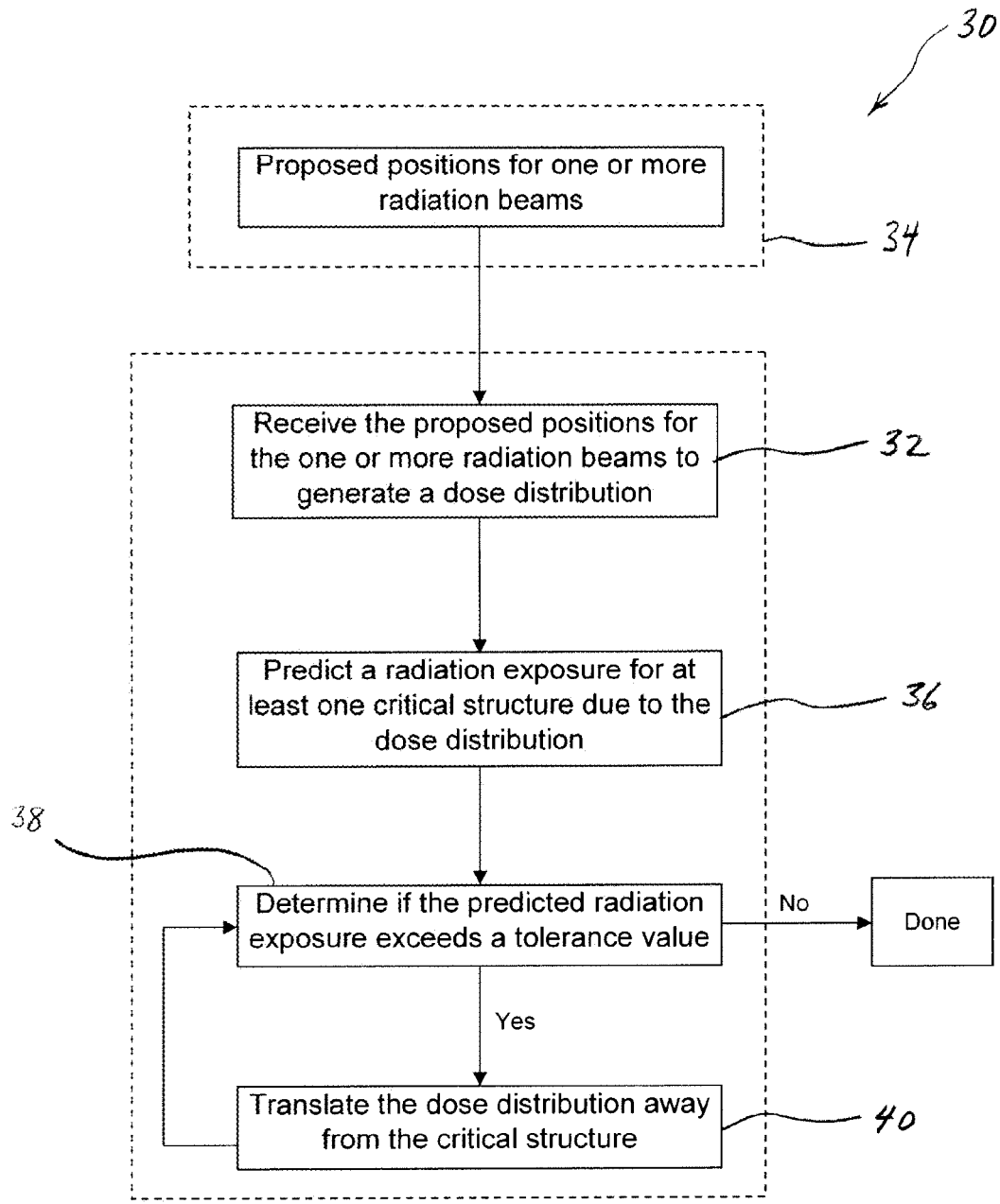
FIG. 5 is a flowchart depicting a method for protecting a critical structure during the administration of radiation treatment to a patient, in accordance with one embodiment of the invention.

Referring to FIG. 5, in certain embodiments, a method 30 is provided for protecting one or more critical structures during the administration of radiation treatment to a patient. The method includes the step of receiving (step 32), from a register 34, proposed positions for one or more radiation beams with respect to at least one critical structure. As described above, the one or more radiation beams define a dose distribution. The method also includes predicting (step 36) a radiation exposure for at least one critical structure based on the dose distribution, and determining (step 38) if the predicted radiation exposure exceeds a tolerance value. If the predicted radiation exposure exceeds the tolerance value, the method 30 includes translating (step 40) the dose distribution with respect to the at least one critical structure until the predicted radiation exposure is below the tolerance value. Steps 32, 36, 38, and 40 may be performed by a processor 42. The register 34 may be any known organized data storage facility (e.g., partitions in RAM, etc.). In certain embodiments, the steps of method 30 are performed by a system that includes the register 34 and the processor 42.

Figure 6:
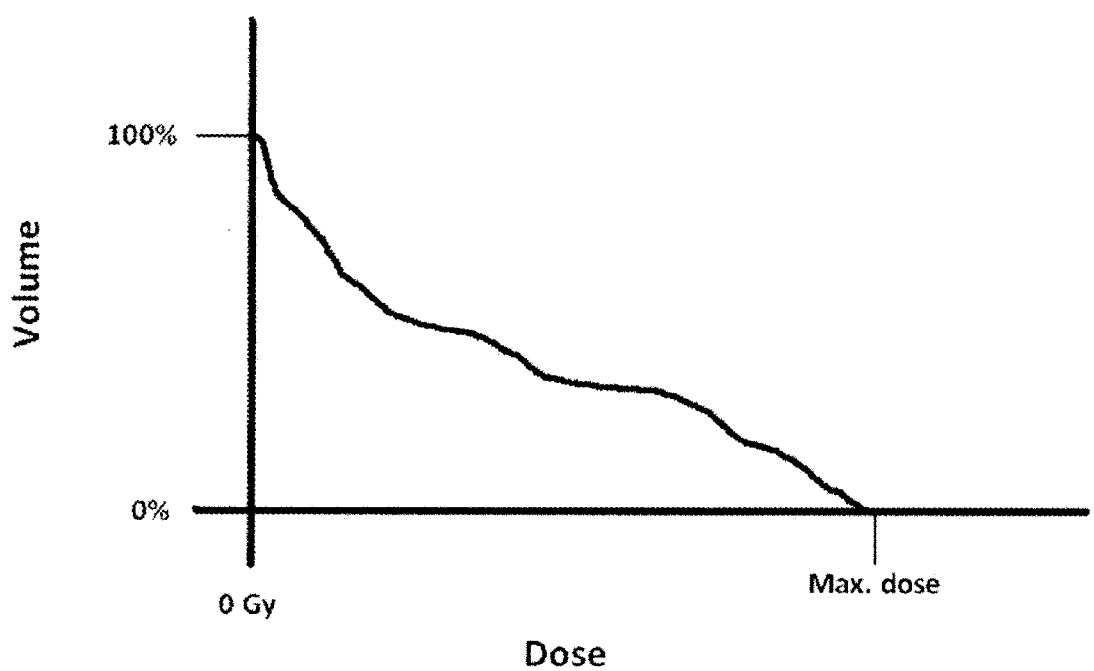
FIG. 6 is a graph of a cumulative dose volume histogram, in accordance with one embodiment of the invention.

In certain embodiments, the predicted radiation exposure and the tolerance value are defined in terms of a cumulative dose volume (CDV). The CDV may be, for example, a percentage of a volume of tissue (e.g., a critical structure) that receives or is predicted to receive a radiation dose higher than a specified value. Referring to FIG. 6, the CDV may be depicted in the form of a cumulative dose volume histogram, which shows CDV as a function of radiation dose.

In one embodiment, the method 30 includes generating an alert indicating that the predicted radiation exposure exceeds the tolerance value. The alert may be, for example, visual (e.g., flashing lights or indicators), audible (e.g., beeps or buzzes), and/or physical (e.g., vibration).

Figure 7:
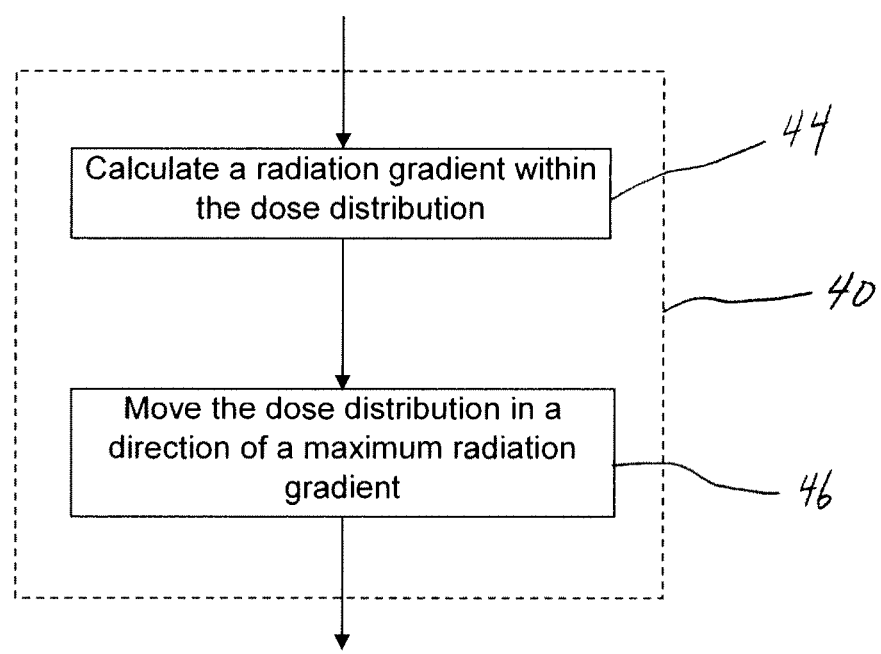
FIG. 7 is a flowchart depicting a portion of a method for protecting a critical structure during the administration of radiation treatment to a patient, in accordance with one embodiment of the invention.

Referring to FIG. 7, the method 30 may also include determining a direction in which to translate the dose distribution away from one or more critical structures. For example, in certain embodiments, the translating step 40 includes the steps of calculating (step 44) a radiation gradient within the dose distribution, and moving (step 46) the dose distribution in a direction of a maximum radiation gradient.

Figure 8:
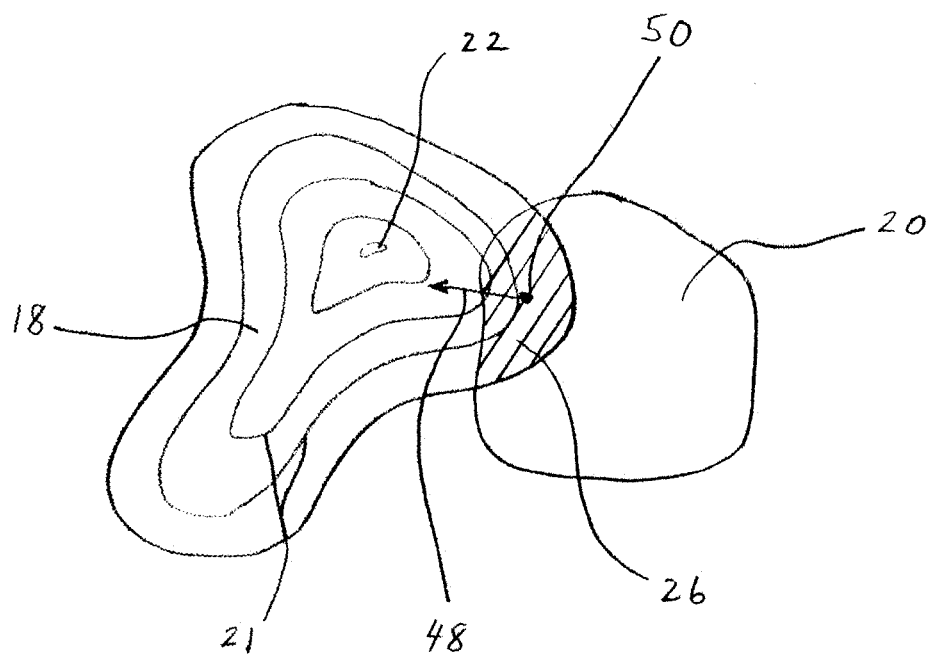
FIG. 8 is a schematic, cross-sectional view of a dose distribution and a critical structure, in accordance with one embodiment of the invention.

Referring to FIG. 8, the dose distribution 18 may include irregularly shaped radiation isocontours 21 surrounding the isocenter 22. Radiation gradients within the dose distribution 18 may be oriented in a direction perpendicular to the isocontours 21. As described above, in one embodiment, the methods and systems are used to identify a maximum radiation gradient 48 within the dose distribution 18. The dose distribution may then be translated in a direction of the maximum radiation gradient 48. In one embodiment, the maximum radiation gradient 48 passes through the isocenter 22 of the dose distribution 18.

As depicted, in certain embodiments, the maximum radiation gradient 48 is located within the region of contact 26 between the dose distribution 18 and the critical structure 20. For example, the processor 42 may be configured to identify the maximum radiation gradient 48 within the region of contact 26 and to translate the dose distribution 18 in a direction defined by the maximum radiation gradient 48. As depicted, the direction of the maximum radiation gradient 48 may pass through or be located at a point of intercept 50, which may be any point within the region of contact 26 between the dose distribution 18 and the critical structure 20. For example, the point of intercept 50 may be at a center of the region of contact 26. In other embodiments, the point of intercept 50 is at a location of greatest overlap between the dose distribution 18 and the critical structure 20, and/or at a location of maximum radiation exposure within the critical structure 20.

By moving the dose distribution 18 in the direction of the maximum radiation gradient 48, the methods and systems described herein are advantageously capable of reducing the radiation exposure (e.g., CDV) to one or more critical structures in an efficient manner. For example, the direction of the maximum radiation gradient 48 may be the direction in which a given distance of translation of the dose distribution 18 will produce the greatest reduction in radiation exposure to the critical structure 20.

In certain embodiments, the radiation gradient (also referred to as the radiation intensity gradient) at any point within a dose distribution is a vector that points in the direction of the greatest rate of increase in radiation intensity, and whose magnitude is the greatest rate of change. For example, if the dose distribution has a radiation intensity R, the radiation gradient at any x, y, z location within the dose distribution may be determined from $$\nabla R(x, y, z) = \left(\frac{\partial R}{\partial x}, \frac{\partial R}{\partial y}, \frac{\partial R}{\partial z}\right).$$

Partial derivatives of R with respect to x, y, and z may be determined numerically using techniques (e.g., finite differences) that are well known in the art.

Figure 9:
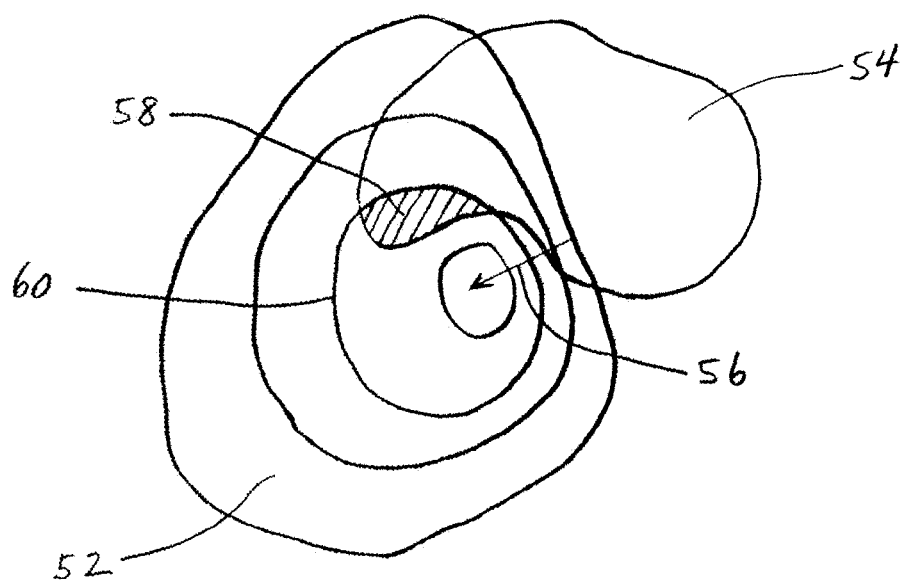
FIG. 9 is a schematic, cross-sectional view of a dose distribution and a critical structure, in accordance with one embodiment of the invention.

Depending on the shapes and sizes of the critical structure and the dose distribution, however, the direction of maximum radiation gradient may not be the best or most efficient direction in which to translate the dose distribution. For example, FIG. 9 depicts a two-dimensional representation of a dose distribution 52 and a critical structure 54. A maximum radiation gradient is indicated by a vector 56 in this figure. The critical structure 54 is predicted to receive a high dose of radiation in a region 58 defined by an isocontour 60. As depicted, given the shapes and positions of the critical structure 54 and the dose distribution 52, vector 56 may not define the best direction in which to translate the dose distribution 52. Specifically, translating the dose distribution 52 along vector 56 would not efficiently reduce the size of the region 58. As a result, an excessive amount of translation may be required to satisfy the tolerance value, which may cause the target to receive less than a desired dose.

To identify a more efficient direction in which to translate the dose distribution 50, in another embodiment, the dose distribution 50 is translated according to a relationship between the CDV for the critical structure 54 and the position of the dose distribution 50. Specifically, the relationship may be used to identify a direction that requires the least amount of translation before the CDV satisfies the tolerance value. By following this approach, the direction of translation may take into account both the radiation gradient within the dose distribution 50 and the shapes and sizes of the critical structure 54 and the dose distribution 52.

Figure 10:
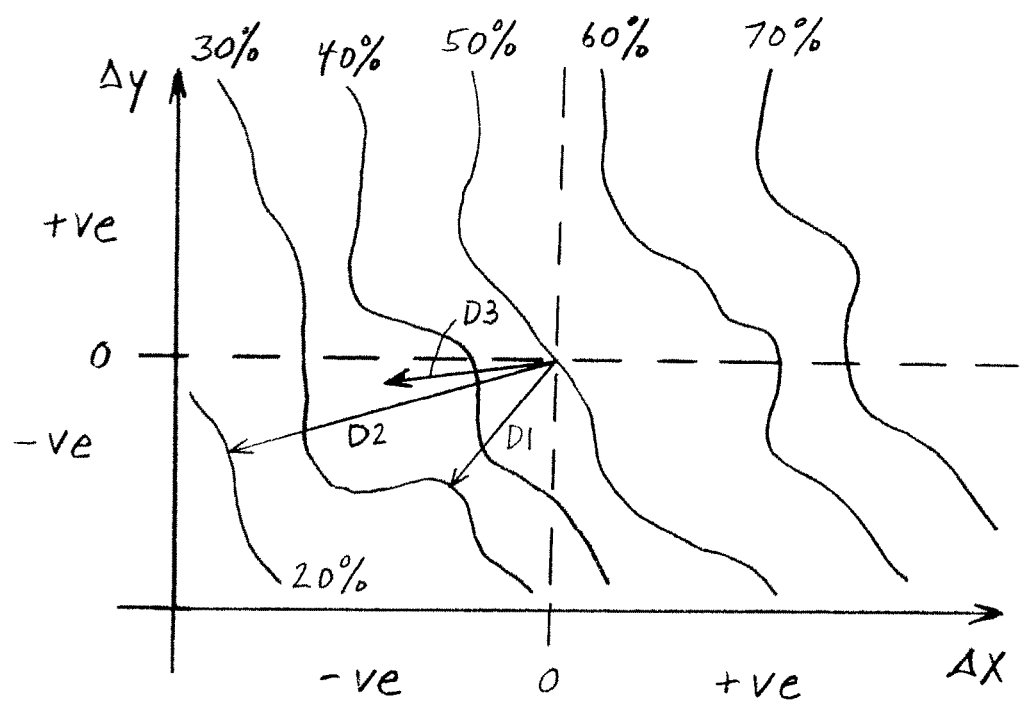
FIG. 10 is a two-dimensional plot of a relationship between cumulative dose volume and a position of a dose distribution, in accordance with an embodiment of the invention.

FIG. 10 is a two-dimensional plot showing a relationship between CDV and the position of a dose distribution, in accordance with an embodiment of the invention. The figure depicts CDV iso-percentages of 20%, 30%, 40%, 50%, 60%, and 70% as a function of displacement (i.e., $\Delta x$ and $\Delta y$) of the dose distribution from its current position (i.e., $\Delta x=0$ and $\Delta y=0$). Although the relationship is shown as two-dimensional, this relationship may be, in reality, three-dimensional, with iso-percentages defined by surfaces, rather than two-dimensional curves. In the depicted embodiment, the CDV is 50% at zero displacement. Stated differently, at the current position of the dose distribution, 50% of the critical structure will receive a radiation dose greater than the specified value, which may be, for example, 20 Gy.

In one embodiment, it may be desirable to reduce the CDV for the critical structure from 50% to 30%. As depicted, a desired translation direction for achieving the 30% CDV may be direction D1, which is a direction in which the 30% iso-percentage curve may be reached with the least amount of displacement. For comparison purposes, the direction requiring the least amount of displacement to reach the 20% iso-percentage curve is direction D2.

Figure 11:
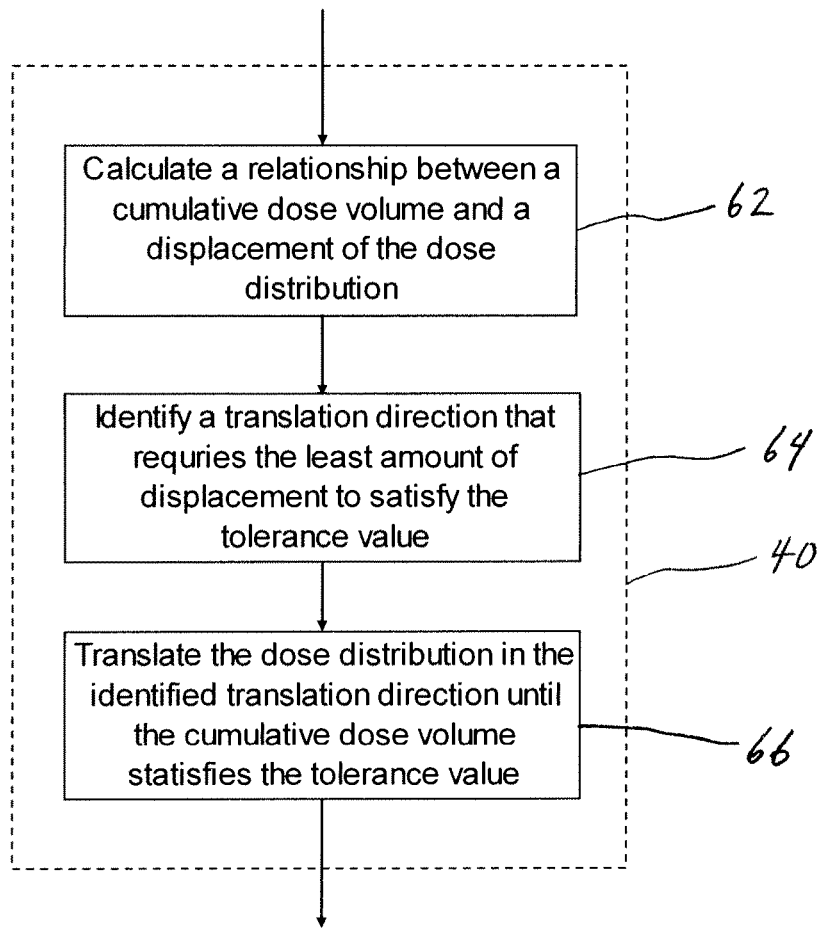
FIG. 11 is a flowchart depicting a portion of a method for protecting a critical structure during the administration of radiation treatment to a patient, in accordance with one embodiment of the invention.

Referring to FIG. 11, in one embodiment, the translation step 40 of the method 30, described above, includes calculating (step 62) a relationship between the CDV and the position of the dose distribution. The relationship may be calculated analytically and/or numerically. For example, the dose distribution may be moved to various proposed locations in the x, y, and z directions, and the CDV may be calculated at each proposed location. Iso-percentages may be obtained by fitting curves or surfaces through the calculated CDV values. As described above, the method 30 may also include identifying (step 64) a translation direction that requires the least amount of displacement of the dose distribution before the CDV satisfies the tolerance value. Once the desired direction for translating the dose distribution has been identified, the method 30 may also include translating (step 66) the dose distribution in the desired direction until the CDV satisfies the tolerance value.

Figure 12:
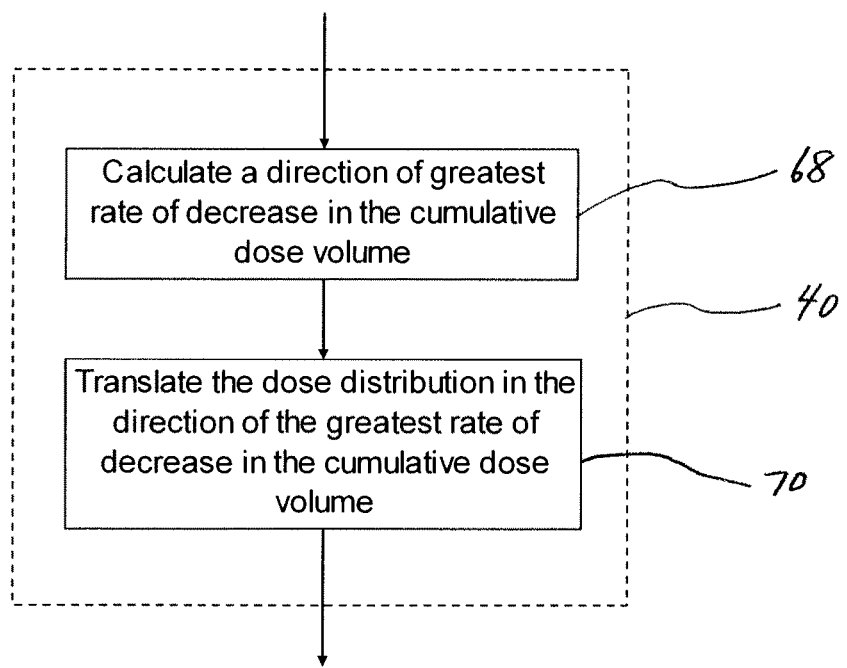
FIG. 12 is a flowchart depicting a portion of a method for protecting a critical structure during the administration of radiation treatment to a patient, in accordance with one embodiment of the invention.

Referring to FIG. 12, in another embodiment, the CDV received by the critical structure is reduced by displacing the dose distribution in a direction of greatest rate of decrease in the CDV. Specifically, the translating step 40 of method 30 may include calculating (step 68) a direction of greatest rate of decrease in the CDV, and translating (step 70) the dose distribution in this direction. In the embodiment depicted in FIG. 10, the direction of greatest rate of decrease in the CDV may be direction D3. In one embodiment, the dose distribution is translated in direction D3 to reduce the CDV as quickly as possible while maintaining a desired dose for the target. This approach may be used, for example, when large translations are not desirable and/or when there is no need to reduce the CDV to a certain value. In one embodiment, the direction of greatest decrease in the CDV is aligned with a gradient of the CDV.

In one embodiment, the systems and methods described herein provide a sliding scale that allows an operator to choose how much emphasis to put on maintaining a desired dose to the target, and how emphasis much to put on sparing critical organs. For example, in the embodiment depicted in FIG. 10, if an operator's goal is to reduce the CDV from 50% to 30%, then the dose distribution may be moved along direction D1, which corresponds to the closest point on the 30% iso-percentage line. On the other hand, if the operator's goal is to reduce the CDV as quickly as possible without trying to reach a particular CDV, then the dose distribution may be translated along direction D3, which points in a direction of greatest rate of decrease in CDV. In other embodiments, the dose distribution is moved in a direction that lies between D1 and D3. For example, depending on the value the operator selects on the sliding scale, the system may move the dose distribution along direction D1, direction D3, or in a direction that lies between those two directions.

In another embodiment, the systems and methods may move the dose distribution a small (e.g., differential) amount in the direction of greatest rate of decrease in CDV. Once the dose distribution has been relocated, a new direction of greatest rate of decrease in CDV may be calculated, and the dose distribution may be displaced again a small amount in that new direction. This process of calculating the greatest rate of decrease in CDV and translating the dose distribution in that direction may be repeated a desired number of times. For example, the process may be repeated until the CDV reaches the tolerance value. This approach may be capable of identifying the least amount of translation required to achieve a specified tolerance value.

In certain embodiments, the systems and methods described herein attempt to satisfy more than one tolerance value. For example, the patient situation may include multiple critical structures, each having their own radiation exposure tolerance values. For example, one critical structure may be a spinal cord having a low exposure tolerance, and another critical structure may be a liver having a relatively high exposure tolerance. The patient situation may also include a target (e.g., a tumor) having a minimum dose tolerance. In one embodiment, a goal of a treatment planning system is to produce a treatment plan that satisfies these multiple tolerance values.

Figure 13:
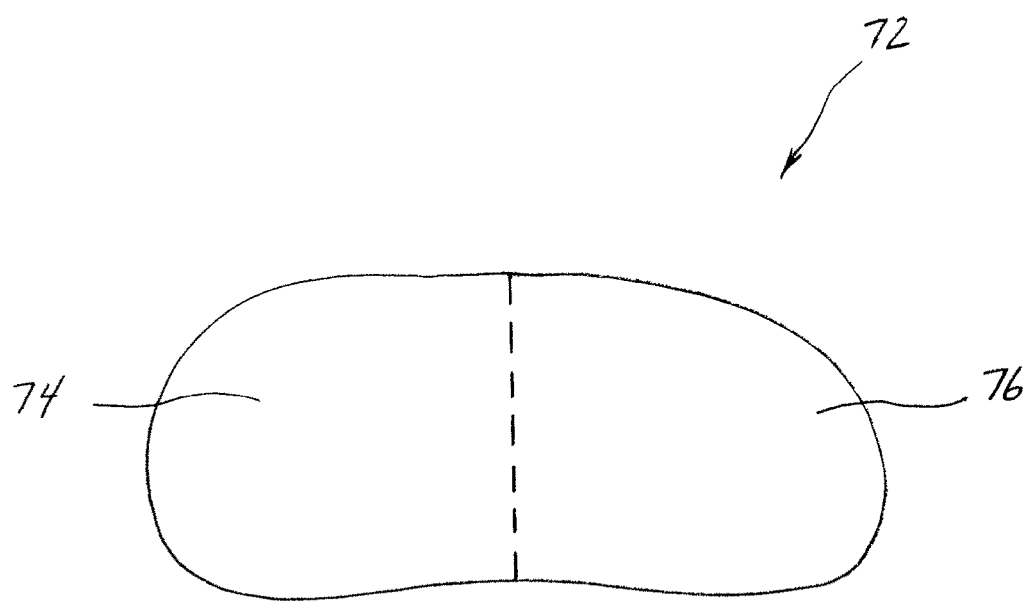
FIG. 13 is a schematic view of a critical structure having a more sensitive portion and a less sensitive portion, in accordance with one embodiment of the invention.

In another embodiment, the CDV of a critical structure is weighted according to variations within the critical structure. For example, the critical structure may have a portion that is more sensitive to radiation, and another portion that is less sensitive to radiation. To better protect the more sensitive portion, the CDV may be weighted such that radiation exposure to the more sensitive portion disproportionately increases the CDV. To illustrate this concept, FIG. 13 depicts a critical structure 72 in which half of the critical structure is a more sensitive portion 74, and the other half of the critical structure is a less sensitive portion 76. In a hypothetical treatment plan, the CDV of the more sensitive portion 74 may be 60%, and the CDV of the less sensitive portion 76 may be 40%. Without weighing the CDVs of the two portions 74, 76 differently, the CDV for the critical structure 72 is 50% (i.e., the average of 40% and 60%). If weights are applied, however, the CDV for the more sensitive portion 74 is weighed more heavily than the CDV for the less sensitive portion 76, and the CDV for the critical structure 72 is greater than 50%. The higher CDV for the critical structure 72 protects the more sensitive portion 72 by requiring a greater reduction in CDV to satisfy the tolerance value. In one embodiment, the relationship between CDV and the position of the dose distribution, as described above and depicted in FIG. 10, is determined using a weighted CDV.

In certain embodiments, the methods and systems provided herein translate the dose distribution in an iterative manner. For example, with each iteration, the dose distribution may be translated by a translation distance, and the radiation exposure to the critical structure may be recalculated based on the new location of the dose distribution. If the radiation exposure is still excessive (e.g., above an acceptable threshold value), the dose distribution may be translated again by the translation distance. In one embodiment, the translation distance may be any distance that is capable of achieving a reduction of the radiation exposure to the critical structure. The translation distance may be a fixed value, or it may vary. For example, the translation distance may change from one iteration to the next, and/or it may change from one patient situation to the next, depending on the sizes and relative positions of the target and any critical structures. In one embodiment, the translation distance is a function of the radiation exposure to the critical structure. For example, when the radiation exposure is large, the translation distance may be large. When the radiation exposure is small, the translation distance may be small. The translation distance may be proportional to a difference between the radiation exposure and the acceptable threshold value. Typical translation distances may be, for example, about 5 cm, about 1 cm, about 0.5 cm, about 1 mm, or about 0.1 mm.

In certain embodiments, the methods and systems described herein interface with a device that administers radiation to the patient. For example, a dose distribution identified by the methods and systems may be conveyed to the device, and the device may then expose the patient to radiation according to the dose distribution.

The device used to administer the radiation may be any device capable of delivering a beam of radiation for radiation treatment. The device may include a single radiation source that is capable of moving with respect to the patient to deliver one or more doses at different positions and orientations. Alternatively, the device may include multiple radiation sources that are capable of delivering multiple radiation beams to the patient simultaneously.

Figure 14:
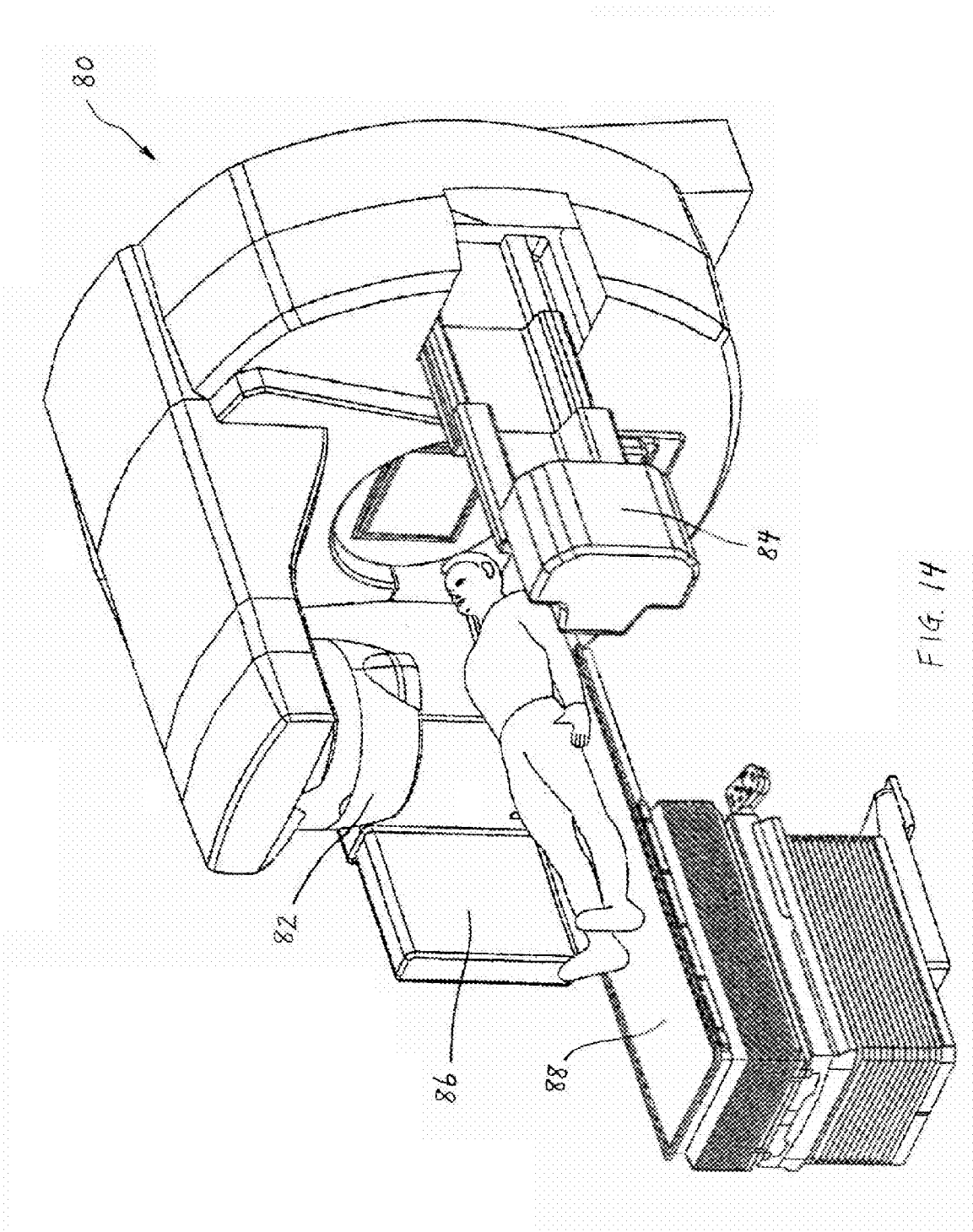
FIG. 14 is a schematic, perspective view of a device for administering radiation to a patient, in accordance with one embodiment of the invention.

Referring to FIG. 14, in one embodiment, a treatment device 80 includes a radiation source 82 that may be positioned around the patient at various angles. The treatment device 80 may also include an imaging system to obtain scans of the patient situation, including the sizes, shapes, and positions of any tumors and critical structures. As depicted, the imaging system may include an x-ray source 84 and an x-ray image detector (imager) 86. In one embodiment, for example, the x-ray source 84 is configured to project x-ray beams through a patient positioned on a treatment couch 88. The x-ray beams may be projected from various angular positions (e.g., separated by 90 degrees) and aimed through the patient toward the detector 86. Other numbers and configurations of imaging sources and imagers are contemplated.

Treatment device 80 may be a gantry based (isocentric) intensity modulated radiotherapy (IMRT) system. The radiation source 82 (e.g., a LINAC) may be mounted on a gantry in such a way that it rotates in a plane corresponding to an axial slice of the patient. Radiation may then be delivered from several positions on the circular plane of rotation. In IMRT, the shape of the radiation beam may be defined by a multi-leaf collimator that allows portions of the beam to be blocked, so that the remaining beam incident on the patient has a pre-defined shape. The resulting system may generate arbitrarily shaped radiation beams that intersect each other at an isocenter to deliver a dose distribution to the target.

In certain embodiments, the device is a stereotactic frame system such as the GAMMA KNIFE®, available from Elekta of Sweden. With such a device, the systems and methods provided herein may determine the selection and dose weighting assigned to a group of beams, in order to best meet provided dose constraints.

In other embodiments, the device includes a radiation source mounted on the end of a robotic arm having multiple (e.g., 5 or more) degrees of freedom to position the radiation source at various angles around the patient. The treatment device may include one or more x-ray sources and one or more x-ray image detectors. In one embodiment, for example, the one or more x-ray sources are configured to project x-ray beams through the patient from two different angular positions.

In some embodiments, the register and processor may implement the functionality of the present invention in hardware or software, or a combination of both on a general-purpose computer. In addition, such a program may set aside portions of a computer's random access memory to provide control logic that affects one or more of the image manipulation, fusion, alignment, and support device control. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for protecting a critical structure during the administration of radiation treatment to a patient, the method comprising the steps of:
   (a) receiving, from a register, proposed positions for one or more radiation beams with respect to a critical structure, wherein a combination of the one or more radiation beams defines a dose distribution having a dose distribution position; and
   at a processor,
   (b) predicting a cumulative dose volume for the critical structure based on the dose distribution, wherein the cumulative dose volume comprises a volume of the critical structure that is predicted to receive more than a specified radiation dose;
   (c) determining if the cumulative dose volume exceeds a tolerance value; and
   (d) if the cumulative dose volume exceeds the tolerance value, translating the dose distribution at least in part based on a relationship between the cumulative dose volume and the dose distribution position.

2. The method of claim 1, wherein the translating step comprises determining a direction in which to translate the dose distribution with respect to the critical structure, wherein the direction requires a minimum amount of translation to achieve a cumulative dose volume equal to the tolerance value.

3. The method of claim 2, wherein the translating step comprises translating the dose distribution in the direction until the cumulative dose volume is equal to the tolerance value.

4. The method of claim 1, wherein the translating step comprises translating the dose distribution in a direction of a greatest rate of decrease in cumulative dose volume.

5. The method of claim 1, wherein the translating step comprises translating the dose distribution in a hybrid direction, wherein the hybrid direction lies between (i) a direction requiring a minimum amount of translation to achieve a cumulative dose volume equal to the tolerance value, and (ii) a direction of a greatest decrease in cumulative dose volume.

6. The method of claim 1, wherein the relationship is determined by translating the dose distribution to proposed locations and calculating the cumulative dose volume at each proposed location.

7. The method of claim 1, wherein, subsequent to translating the dose distribution, the dose distribution intersects the critical structure.

8. The method of claim 1, comprising the step of generating an alert indicating that the predicted radiation exposure exceeds the tolerance value.

9. The method of claim 1, wherein the tolerance value is greater than zero.

10. A system for protecting a critical structure during the administration of radiation treatment to a patient, the system comprising:
    (a) a register configured to store proposed positions for one or more radiation beams with respect to at least one critical structure, wherein a combination of the one or more radiation beams defines a dose distribution having a dose distribution position; and
    (b) a processor configured to:
      (i) predict a cumulative dose volume for the critical structure based on the dose distribution, wherein the cumulative dose volume comprises a volume of the critical structure that is predicted to receive more than a specified radiation dose;
      (ii) determine if the cumulative dose volume exceeds a tolerance value; and
      (iii) if the cumulative dose volume exceeds the tolerance value, translate the dose distribution at least in part based on a relationship between the cumulative dose volume and the dose distribution position.

11. The system of claim 10, wherein the processor is configured to determine a direction in which to translate the dose distribution with respect to the critical structure, wherein the direction requires a minimum amount of translation to achieve a cumulative dose volume equal to the tolerance value.

12. The system of claim 11, wherein the processor is configured to translate the dose distribution in the direction until the cumulative dose volume is equal to the tolerance value.

13. The system of claim 10, wherein the processor is configured to translate the dose distribution in a direction of a greatest rate of decrease in cumulative dose volume.

14. The system of claim 10, wherein the processor is configured to translate the dose distribution in a hybrid direction, wherein the hybrid direction lies between (i) a direction requiring a minimum amount of translation to achieve a cumulative dose volume equal to the tolerance value, and (ii) a direction of a greatest decrease in cumulative dose volume.

15. The system of claim 10, wherein, to determine the relationship, the processor is configured to translate the dose distribution to proposed locations and calculate the cumulative dose volume at each proposed location.

16. The system of claim 10, wherein, subsequent to translation of the dose distribution, the dose distribution intersects the critical structure.

17. The system of claim 10, wherein the processor is further configured to generate an alert indicating that the predicted radiation exposure exceeds the tolerance value.

18. The system of claim 10, wherein the tolerance value is greater than zero.

* * * * *